United States Patent

Seto et al.

[11] Patent Number: 5,874,048
[45] Date of Patent: Feb. 23, 1999

[54] SPOTTING TIP

[75] Inventors: Shunichi Seto, Kanagawa-ken; Kenichiro Yazawa; Osamu Seshimoto, both of Saitama-ken, all of Japan

[73] Assignee: Fuji Photo Film Co., Ltd., Kanagawa-ken, Japan

[21] Appl. No.: 906,006

[22] Filed: Aug. 4, 1997

Related U.S. Application Data

[63] Continuation of Ser. No. 527,374, Sep. 13, 1995.

[30] Foreign Application Priority Data

Sep. 16, 1994 [JP] Japan ................................. 6-221762

[51] Int. Cl.⁶ ....................................................... B01L 3/02
[52] U.S. Cl. ........................... 422/100; 422/58; 422/68.1; 422/99; 422/102; 422/104; 73/864.22; 73/864.23; 73/864.24; 73/864.25; 215/247; 215/248; 215/309; 215/310; 215/355
[58] Field of Search ............................... 422/58, 68.1, 99, 422/100, 102, 104; 73/864.22, 864.23, 864.24, 864.25; 215/247, 248, 309, 310, 355

[56] References Cited

U.S. PATENT DOCUMENTS

| | | | |
|---|---|---|---|
| 1,920,335 | 8/1933 | Wood | 215/58 |
| 4,210,255 | 7/1980 | Pan | 215/310 |
| 4,478,095 | 10/1984 | Bradley et al. | 73/864.23 |
| 4,648,519 | 3/1987 | Kennedy | 215/261 |
| 4,713,974 | 12/1987 | Stone | 73/864.23 |
| 4,787,898 | 11/1988 | Raines | 604/411 |
| 5,036,992 | 8/1991 | Mouchawar et al. | 215/247 |
| 5,038,958 | 8/1991 | Drier | 215/355 |
| 5,078,970 | 1/1992 | Teodorescu et al. | 422/100 |
| 5,188,628 | 2/1993 | Rani et al. | 215/248 |
| 5,232,109 | 8/1993 | Tirrell et al. | 215/247 |
| 5,240,679 | 8/1993 | Steller | 73/864.24 |
| 5,336,468 | 8/1994 | Tezuka et al. | 422/100 |
| 5,483,843 | 1/1996 | Miller et al. | 73/864.23 |

FOREIGN PATENT DOCUMENTS 0331057  9/1989  European Pat. Off. .

OTHER PUBLICATIONS

Patent Abstracts of Japan, vol. 018 No. 525, Oct. 5, 1994, & JP–A–06 182234 (Aloka Co., Ltd.) Jul. 5, 1994;.
Patent Abstracts of Japan, Vo. 950, No. 003, & JP–A–07 080331 Fuji Photo Film Co., Ltd, Mar. 28, 1995.

*Primary Examiner*—Jill Warden
*Assistant Examiner*—S. Carrillo
*Attorney, Agent, or Firm*—McAulay Nissen, Goldberg Kiel & Hand, LLP

[57] ABSTRACT

A spotting tip includes a tip body which is fitted on the end of a nozzle for sucking liquid contained in a container and inserted into the liquid in the container through a mouth of the container, and a lid member which is brought into contact with the mouth of the container and closes the space between the tip and the edge of the mouth when the tip is inserted into the container to a predetermined depth. At least one fine communicating passage is formed in at least one of the lid member and the tip body to communicate the inside and outside spaces of the container on opposite sides of the lid member.

7 Claims, 8 Drawing Sheets

FIG. 9B ized.

SPOTTING TIP

This is a continuation of application Ser. No. 08/527,374, filed Sep. 13, 1995, now abandoned.

BACKGROUND OF THE INVENTION

1. Field of the Invention

This invention relates to a spotting tip which is fitted on a liquid sucking nozzle for sucking liquid in a container, and more particularly to a spotting tip which sucks liquid to be subjected to a biochemical analysis or the like and spots the liquid on an element, device or the like for biochemical analysis.

2. Description of the Related Art

Quantitative analysis of a particular chemical component in a sample liquid is commonly carried out in various industrial fields. For example, there have been known various methods of potentiometrically analyzing an activity (or concentration) of a particular ionic substances contained in a spotted sample liquid such as liquors, beverages, city water or a body fluid such as blood, urine or saliva. Ionic activity measuring devices for measuring an activity of an ionic substance in a spotted sample liquid are disclosed, for instance, in Japanese Unexamined Patent Publication Nos. 59(1984)-30055 and 6(1994)-66759, and U.S. Pat. No. 4,437,973.

Generally such an ionic activity measuring device includes at least a set of ion selective electrode pair each having an outermost layer composed of an ion selective layer which selectively responds to a particular ion such as Na, K, Cl or the like. The ion selective electrode pair are supported between an upper frame and a lower support frame, and a pair of liquid spotting holes are provided in the upper frame respectively opposed to the electrodes. A porous bridge which establishes an electrical connection between a sample liquid spotted to one of the spotting holes and a reference liquid spotted to the other spotting hole is provided in the upper frame. Preferably the porous bridge is formed of twisted yarn of fibers.

In such an ionic activity measuring device, when a reference liquid containing therein an ionic substance whose ionic activity is known is spotted to one of the spotting holes and a sample liquid containing therein the ionic substance whose ionic activity is unknown is spotted to the other spotting hole, the liquids soak into porous liquid distributing members and reach the corresponding ion selective electrodes while the interfaces of the liquids are brought into an electrical contact with each other near the middle of the porous bridge. As a result, there is produced a potential difference between the electrodes according to the difference between the activity of the ionic substance in the sample liquid and that in the reference liquid. By measuring the potential difference, the activity of the ionic substance in the sample liquid can be determined on the basis of a calibration curve or a standard curve which has been determined in advance on the basis of Nernst equation.

The ionic activity measuring device is very useful for analysis of aqueous sample liquid, especially for clinical analysis of a sample liquid from a human body such as blood since the ionic activity can be easily determined by only spotting droplets of the sample liquid and the reference liquid.

When spotting the sample liquid and the reference liquid, the liquids are sucked in different spotting tips and dropped onto the respective spotting holes from the ends of the tips. Each tip is fitted on a liquid sucking nozzle and dipped into the sample liquid or the reference liquid and then the sample liquid or the reference liquid is sucked into the tip in a predetermined amount in response to a sucking operation of the liquid sucking nozzle and then held there. Then the tips on the sucking nozzles are moved to predetermined positions above the ionic activity measuring device and then discharge the sample liquid and the reference liquid onto the spotting holes in response to a discharging operation of the nozzles. The sample liquid and the reference liquid may be spotted either simultaneously or in sequence generally within 60 seconds.

In the container containing the sample liquid or the reference liquid, when the mouth of the container through which the spotting tip is inserted into the container is kept open for a long time, there is a possibility of the liquid evaporating to change the concentrations of the components and spoiling.

Accordingly conventionally the mouth of the container is normally covered with a lid and is opened only when the liquid therein is to be sucked. The lid is put on again immediately thereafter.

However shutting and opening the mouth is very troublesome and puts an obstacle in automating the liquid sucking operation.

In order to overcome the problem, we have proposed a novel tip in our Japanese Unexamined Patent Publication No. 7(1995)-80331. The tip is provided with a lid member which is brought into contact with the mouth of the container and closes the space between the tip and the edge of the mouth when the tip is inserted into the container to a predetermined depth. The tip is normally held in the container with the lid member in contact with the mouth except when the liquid in the container is to be spotted, whereby the container is held air-tight and the liquid in the container is suppressed from evaporating and diffusing outside.

However when the tip was actually used, the liquid in the container flowed back into the tip and in extreme case even into the nozzle after the tip was held in the container for a long time. When such a back flow of the liquid occurs, the liquid cannot be spotted in an accurate amount due to liquid remaining in the tip or nozzle and there is a possibility of the concentration of the liquid changing.

Though not clear, the reason why the back flow occurs is considered to be that when the temperature in the container is raised while the container is held air-tight by the lid member for a long time, gases including vapor expand and raise the liquid in the container into the tip or the nozzle.

SUMMARY OF THE INVENTION

In view of the foregoing observations and description, the primary object of the present invention is to provide a spotting tip for aspirating and precision dispensing liquid which can minimize evaporation of the liquid in the container and at the same time can prevent back flow of the liquid into the tip or the nozzle.

Based on the recognition that the back flow of the liquid in the container can be prevented if the pressure difference between the space inside of the container and the space outside of the same on opposite sides of the lid member can be nullified, the present invention accomplishes the above object by forming a fine communicating passage which communicates the inside and the outside of the container in at least one of the lid member and the tip body.

That is, in accordance with the present invention, there is provided a spotting tip comprising a tip body which is fitted on the end of a nozzle of a liquid sucking means for sucking liquid contained in a container and inserted into the liquid in the container through a mouth of the container, and a lid member which is brought into contact with the mouth of the container and closes the space between the tip and the edge of the mouth when the tip is inserted into the container to a predetermined depth, the liquid sucking means operating to suck a predetermined amount of the liquid into the tip body with the tip body held in the liquid, wherein the improvement comprises at least one fine communicating passage which is formed in at least one of the lid member and the tip body to communicate the inside and outside spaces of the container on opposite sides of the lid member.

The lid member may be formed integrally with the tip body. Otherwise the lid member may be formed separately from the tip body and attached thereto.

The tip body and the lid member may be formed of any material so long as it does not modify nor deteriorate the liquid in the container. For example, the tip body may be formed of an organic polymer material such as polyethylene, polypropylene, fluoropolymer, silicone resin or the like. The lid member may be formed of an organic polymer material such as polyethylene, polypropylene, fluoropolymer, silicone resin or the like or a rubber material such as silicone rubber.

The fine communicating passage may be of any shape and any size so long as it can nullify the pressure difference between the space inside of the container and the space outside of the same on opposite sides of the lid member without largely deteriorating the function of the lid member to suppress evaporation of the liquid in the container. Further a plurality of the fine communicating passages may be provided unless the function of the lid member to suppress evaporation of the liquid in the container is largely deteriorated. However, in order to enhance the function of the lid member, it is preferred that the communicating passage be long to a certain extent. Further when there is only one communicating passage, communication between the inside and outside spaces can be broken if the passage is blocked with foreign matter such as dust, fine cuttings of the lid member or the like or by accident. Accordingly preferably a plurality of the fine communicating passage are be provided.

With the arrangement described above, the container can be held air-tight and the liquid in the container is suppressed from evaporating and diffusing outside the container by normally holding the tip body in the container with the lid member in contact with the mouth of the container, whereby the liquid is prevented from being concentrated. Further since the ingress of foreign matters is prevented, the liquid in the container can be prevented from being contaminated and spoiling. Accordingly, even in a biochemical analysis where a fine change in the concentration of the components gives rise to a problem, the accuracy of measurement can be held high.

Further since the fine communicating passage equalizes the pressures inside and outside the container, the liquid in the container cannot flow into the tip body or the nozzle even if the tip body is held inside the liquid with the lid member in contact with the mouth of the container for a long time. Accordingly the liquid can be constantly spotted in an accurate amount and the change in the concentration of the liquid due to back flow can be prevented.

Further since the mouth of the container is opened and closed by the spotting tip itself, necessity of putting on and off the lid as in the conventional system can be eliminated and the spotting operation is facilitated.

It is preferred that the outer surface of the tip near the liquid intake/discharge port thereof be subjected to a water-repellent treatment or hydrophobicity treatment to prevent the liquid from adhering to the outer surface of the tip body to be carried out, whereby concentration of the liquid in the container is further prevented.

DESCRIPTION OF THE PREFERRED EMBODIMENT

Figure 1:
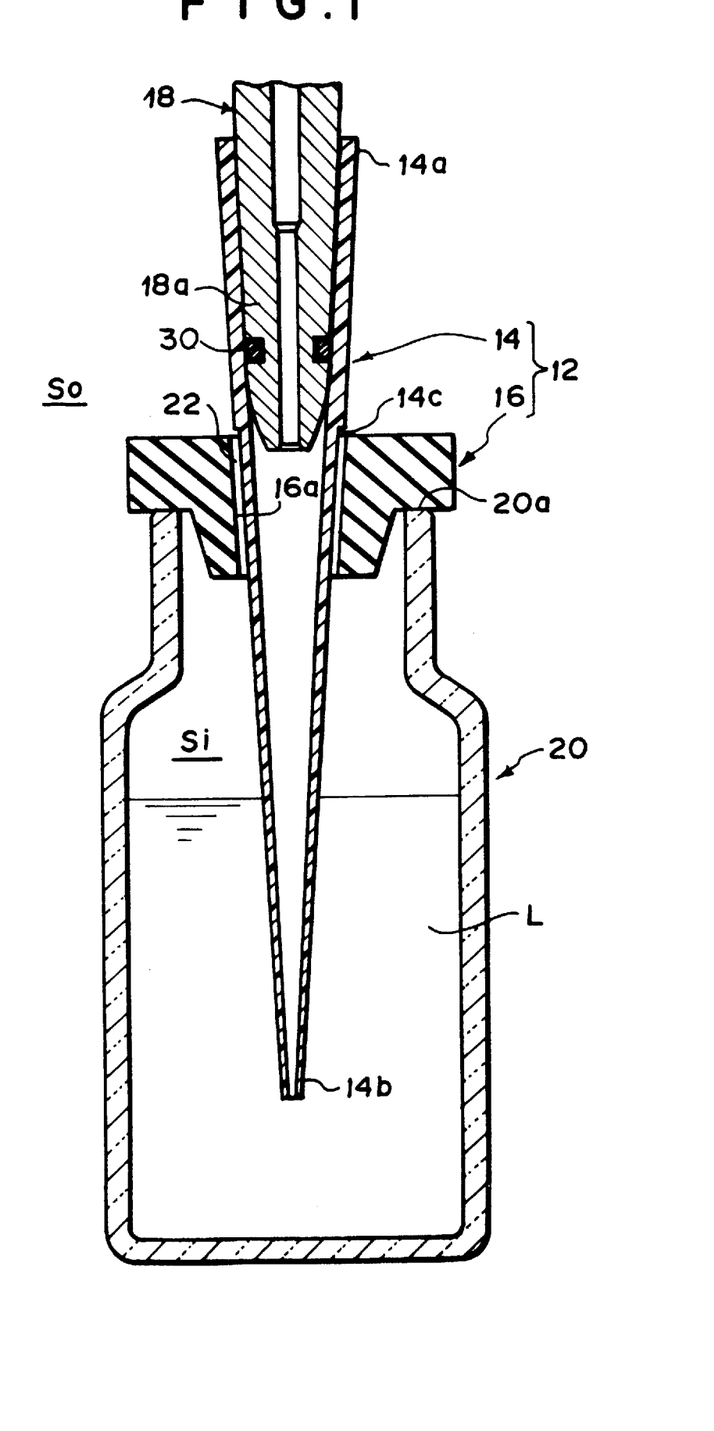
FIG. 1 is a cross-sectional view of a spotting tip in accordance with an embodiment of the present invention with the tip inserted into a container.
Figure 2:
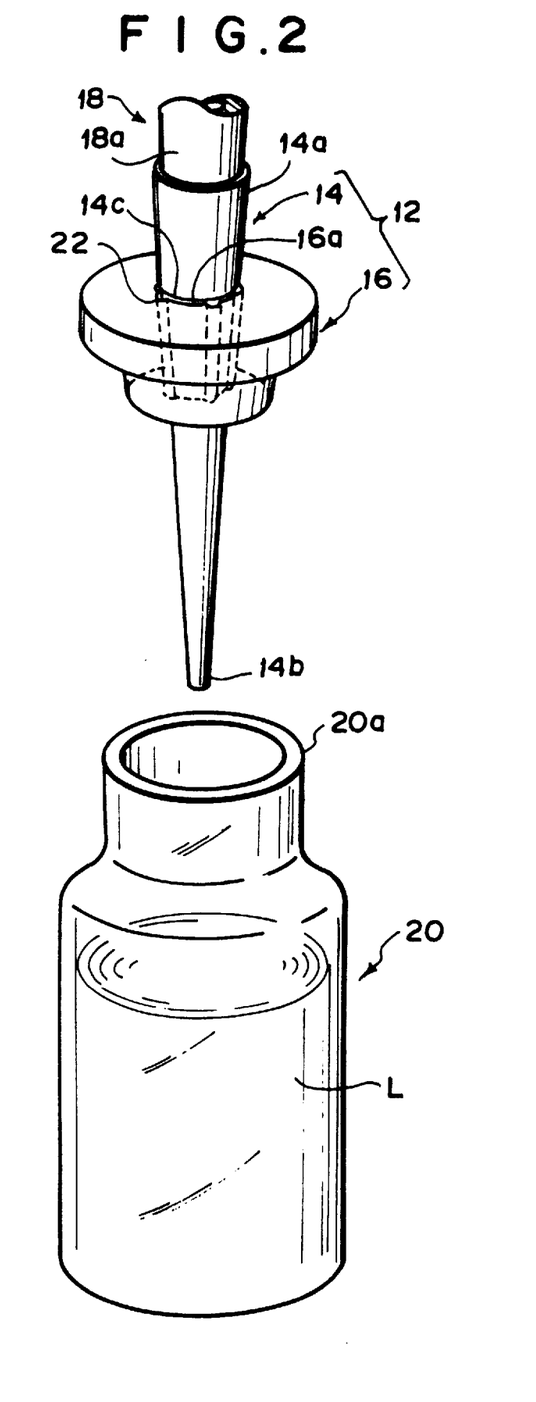
FIG. 2 is a perspective view of the spotting tip away from the container.

In FIGS. 1 and 2, a spotting tip 12 in accordance with an embodiment of the present invention comprises a tip body 14 which is shaped like a cone tapered downward and an annular lid member 16 fitted on the tip body 14 at an intermediate portion thereof.

The spotting tip 12 is mounted on a nozzle 18 of a liquid sucking means (not shown) by press-fitting the upper end portion 14a of the tip body 14 on the lower end portion 18a of the nozzle 18. An O-ring 30 is fitted on the lower end portion 18a of the nozzle 18 and is brought into close contact with the inner peripheral surface of the tip body 14, when the upper end portion 14a of the tip body 14 is fitted on the lower end portion 18a of the nozzle 18, to seal the space between the outer peripheral surface of the nozzle 18 and the inner peripheral surface of the tip body 14 in an air-tight fashion.

A reference liquid L is contained in a container 20 having a mouth 20a. With the spotting tip 12 on the nozzle 18, the tip body 14 is inserted into the container 20 through the mouth 20a so that the lower end portion 14b (having a diameter smaller than the upper end portion 14a) of the tip body 14 is dipped into the reference liquid L. When the reference liquid L is to be spotted, a predetermined amount of the reference liquid L is sucked into the tip body 14 of the spotting tip 12 through the opening at the end of the lower end portion 14b.

The lid member 16 comprises a larger diameter upper portion and a smaller diameter lower portion which is tapered downward. When the tip body 14 is inserted into the container 20 to a predetermined depth, the lower surface of the upper portion of the lid member 16 is brought into contact with the inner peripheral edge of the mouth 20a of the container 20 to shut the space between the mouth 20a and the tip body 14. The lid member 16 is formed of elastic silicone rubber so that the space between the mouth 20a and the tip body 14 is surely shut. Four grooves 16a are formed in the inner peripheral surface 16a of the lid member 16 at intervals of 90° to extend through the lid member 16 in the longitudinal direction thereof. The grooves 22 form four fine communicating passages which communicate the space Si inside the container 20 and the space So outside the container 20 when the spotting tip 12 is inserted into the container 20 so that the lid member 16 closes the mouth 20a. Each groove 16a is semi-circular in cross-section and has a radius of 0.1 to 1.0 mm (e.g., 0.5 mm).

An annular shoulder 14c is formed on the outer peripheral surface of the tip body 14 at an intermediate portion thereof. The shoulder 14c is for limiting the position of the lid member 16 relative to the tip body 14 when the lid member 16 is fitted on the spotting tip 12 and has a width of about 0.3 mm. Even when the tip body 14 is inserted into the lid member 16 until the shoulder 14c is brought into abutment against the lid member 16, the lid member 16 is held away from the shoulder 14c at a distance of about 0.5 to 1.0 mm by virtue of the elasticity (spring back) of the lid member 16. Accordingly the fine communicating passages cannot be closed by the shoulder 14c.

As can be understood from the description above, the container 20 can be held air-tight and the reference liquid L in the container 20 is suppressed from evaporating and diffusing outside the container 20 by normally holding the tip body 14 in the container 20 with the lid member 14 in contact with the mouth 20a of the container 20 except when the liquid L is to be spotted, whereby the liquid L is prevented from being concentrated. Further since the ingress of foreign matters into the container 20 is prevented, the liquid L in the container 20 can be prevented from being contaminated and spoiling. Accordingly, even in a biochemical analysis where a fine change in the concentration of the components gives rise to a problem, the accuracy of measurement can be held high.

Further since the fine communicating passages formed by the grooves 22 on the inner peripheral surface 16a of the lid member 16 communicate the inside space Si and the outside space So and equalize the pressures inside and outside the container, the liquid L in the container 20 cannot flow into the tip body 14 or the nozzle 18 even if the tip body 14 is held inside the liquid L with the lid member 16 in contact with the mouth 20a of the container 20 for a long time. Accordingly the liquid L can be constantly spotted in an accurate amount and the change in the concentration of the liquid L due to back flow can be prevented.

In this particular embodiment, since the fine communicating passages are formed by elongated grooves 22, even if the liquid L evaporates and enters the passages, all most all the vapor is condensed, whereby evaporation of the liquid L outside the container 20 can be effectively prevented.

Thus in accordance with the embodiment described above, evaporation of the reference liquid L outside the container 20 can be minimized and at the same time back flow of the reference liquid L into the tip body 14 or the nozzle 18 can be prevented.

Further since the mouth 20a of the container 20 is opened and closed by the spotting tip 12 itself, necessity of putting on and off the lid as in the conventional system can be eliminated and the spotting operation is facilitated.

Figure 3A:
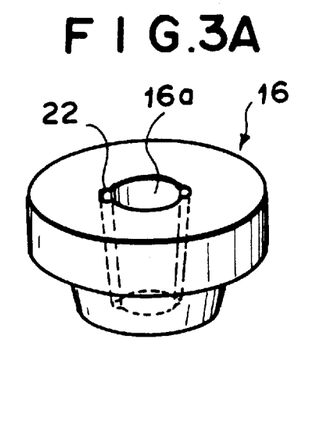
FIGS. 3A, 3B, 4A and 4B are perspective views respectively showing modifications of the lid members employed in the spotting tip of the embodiment.
Figure 3B:
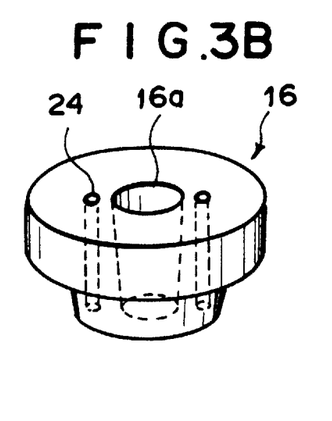

Though, in the embodiment described above, the inside space Si and the outside space So of the container 20 are communicated through the fine communicating passages formed by four grooves 22 which are formed in the inner peripheral surface 16a of the lid member 16 to extend through the lid member 16 in the longitudinal direction thereof and are semi-circular in cross-section, the spaces Si and So may be communicated through only a pair of like grooves 22 as shown in FIG. 3A or through a plurality of (e.g., two or four) through holes 24 formed away from the inner peripheral surface 16a of the lid member 16 as shown in FIG. 3B. In the latter case, the diameter of each through hole may be, for instance, 0.2 to 1.0 mm.

Figure 4A:
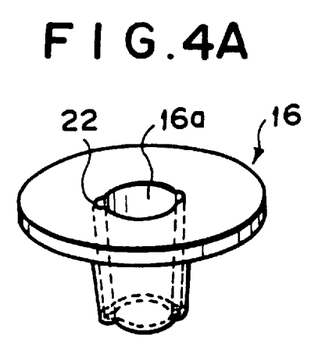
Figure 4B:
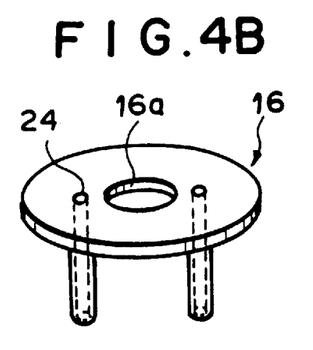
Figure 5:
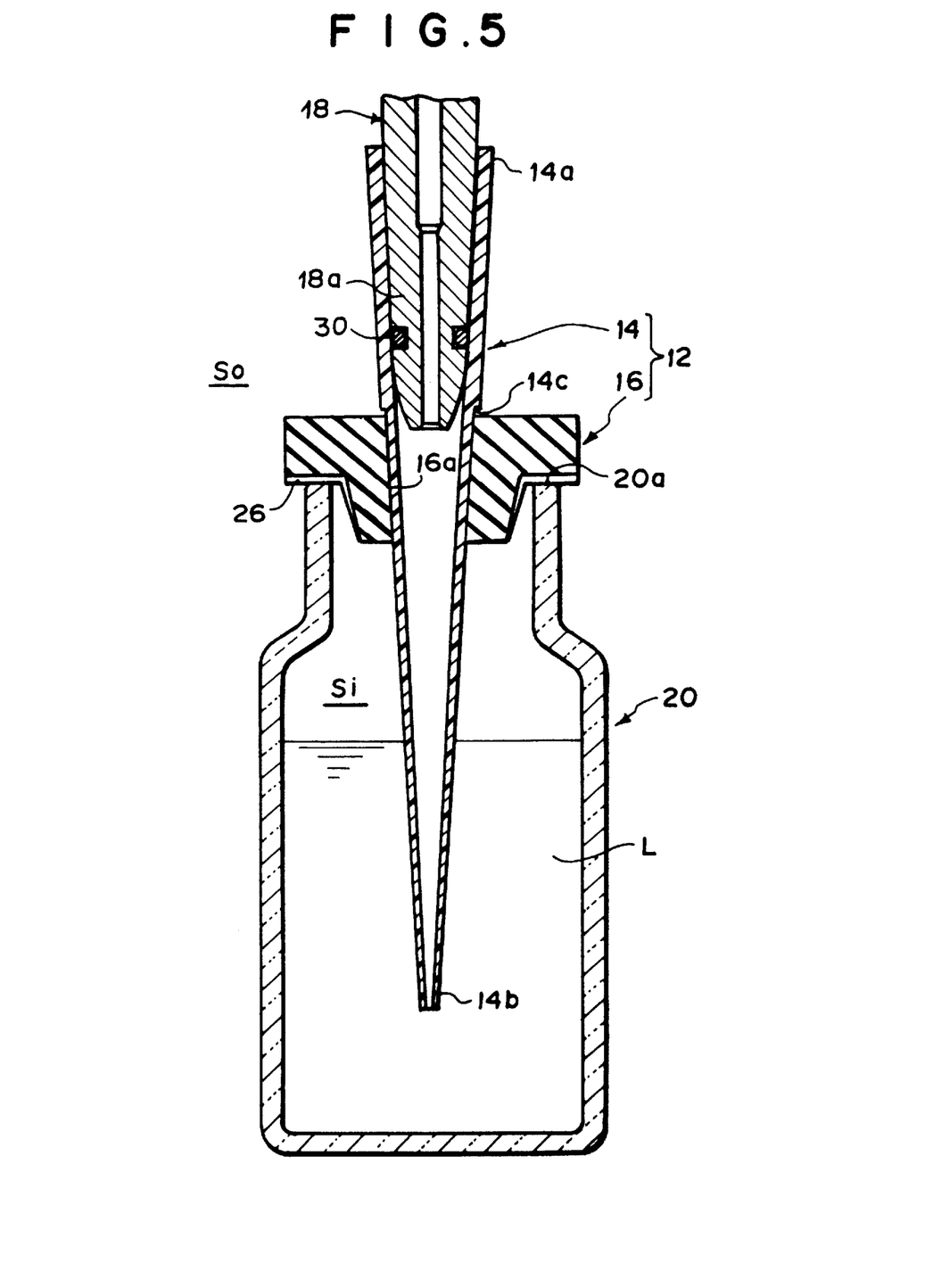
FIGS. 5 and 6 are views similar to FIG. 1 respectively showing modifications of the lid members employed in the spotting tip of the embodiment.

Though the lid member 16 is formed of silicone rubber in the embodiment described above, the lid member 16 may be formed of inexpensive plastic. In this case, the plastic lid member 16 may comprise an annular collar portion and a tubular portion extending downward from the collar portion and semi-circular grooves 22 (e.g., 2 or 4) may be formed along the inner peripheral surface 16a of the tubular portion as shown in FIG. 4A. Further the plastic lid member 16 may comprise an annular collar portion and columns (e.g., 2 or 4) extending downward from the collar portion away from the inner peripheral surface 16a of the lid member 16, and a through hole 24 may be formed in each of the columns to extend therethrough as shown in FIG. 4B. In another modification of the lid member 16 shown in FIG. 5, the communicating passage is formed between the lower surface of the lid member 16 and the upper surface of the mouth 20a of the container 20 by one or more radial grooves formed in the lower surface of the lid member 16.

Figure 6:
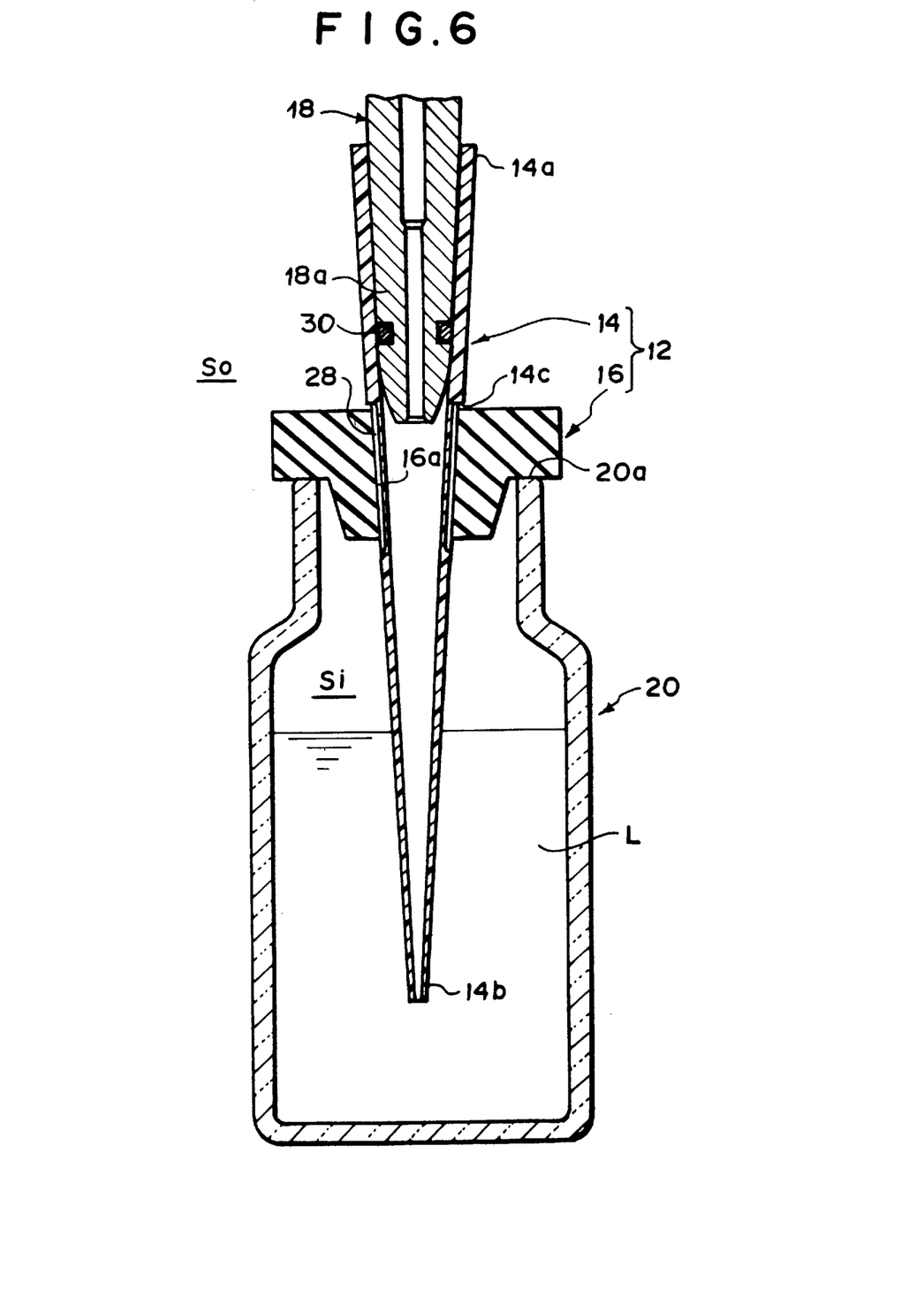

Though in the embodiment and the modifications described above, the communicating passage is formed in the lid member 16, the communicating passage may be formed in the tip body 14. For example, in the modification shown in FIG. 6, the communicating passage is formed by one or more grooves 28 formed on the outer surface of the tip body 14 to extend in the longitudinal direction of the tip body 14 from above the upper surface of the lid member 16 to below the lower surface of the same.

It is preferred that the outer surface (including the bottom surface) of the lower end portion 14b of the tip body 14 near the liquid intake/discharge port thereof be subjected to a water-repellent treatment or hydrophobicity treatment with silicone resin, fluorinated resin, fluorine-containing surface-active agent or the like. Since the tip body 14 is held at a constant height from the bottom of the container 20, the tip body 14 is dipped relatively deep into the reference liquid L when the container 20 contains a large amount of reference liquid L. The water-repellent treatment or hydrophobicity treatment prevents the reference liquid L from adhering to the outer surface of the tip body 14 and being carried out.

The shape of the lid member 16 need not be limited to those described above but may be properly selected according the shape of the tip body 14 and/or the shape of the container 20.

Though in the embodiment described above, the container 20 contains reference liquid L by way of example, the present invention may be applied to containers containing therein various liquids such as sample liquids, reagent solutions and the like.

EXAMPLE 1

Figure 7:
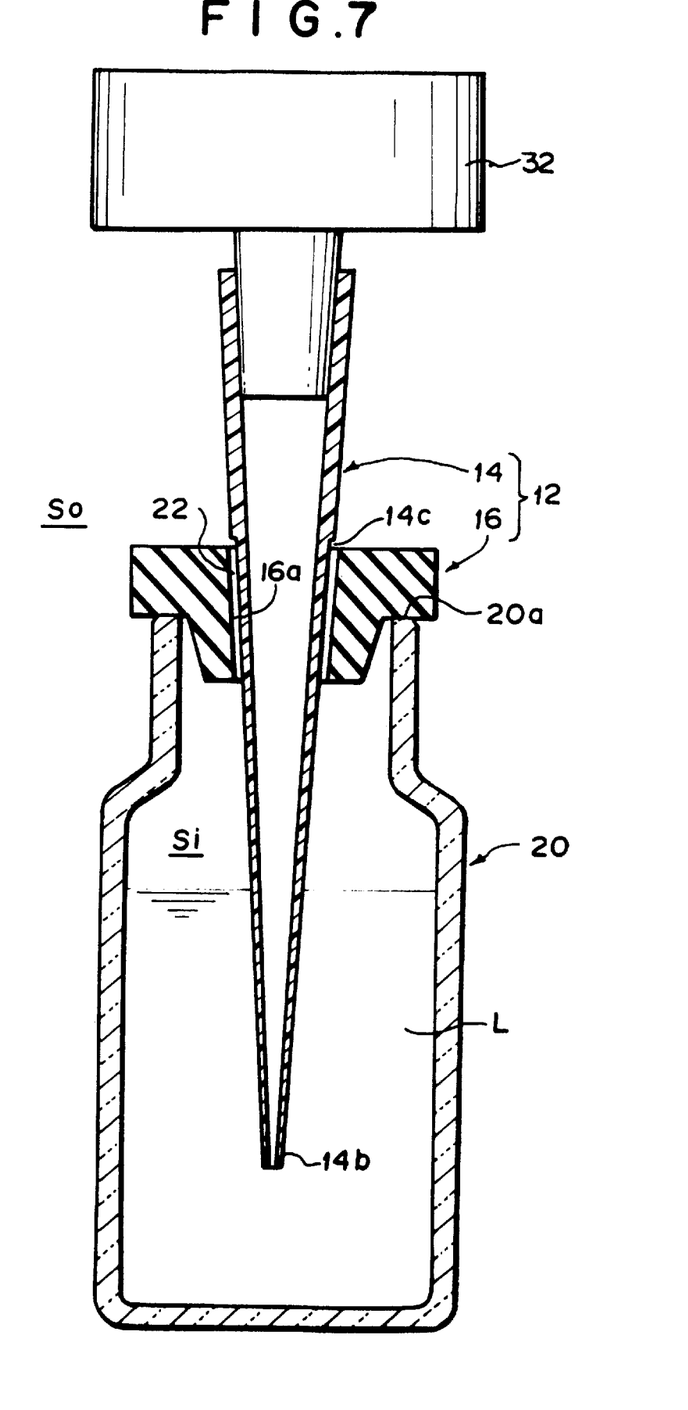
FIG. 7 is a cross-sectional view showing an experimental device which was employed in an experiment for proving the result of the invention.

In order to prove the result of the invention, an experiment was made using an experimental device shown in FIG. 7. In the experiment, the evaporation loss of the reference liquid L in the container 20 was measured.

The experiment was made in the following manner. The spotting tip 12 comprised a tip body 14 formed of polypropylene and a lid member 16 formed of silicone rubber. A container 20 containing therein reference liquid L was prepared and the lid and the inner plug on the container 20 were removed. The spotting tip 12 was inserted into the container 20 through the mouth 20a thereof and the upper open end of the tip body 14 was closed with a weight 32 of 200 g so that the inside space Si and the outside space So of the container 20 were communicated only through the fine communicating passages (grooves 22).

The experimental device was then caused to stand in a room which was kept at a temperature of 32±0.1° C. and a relative humidity of 30±2% for 24 hours. Then reduction in the weight was measured and the evaporation loss was calculated.

FUJI DRI-CHEM ELECTROLYTE REFERENCE FLUID® (trade name) was employed as the reference liquid L. FUJI DRICHEM CLEAN TIPS® (trade name) was used as the tip body 14. The tip was a pipette tip coated with silicone resin on the outer surface of the lower end portion (water-repellent treatment).

Containers 20 each containing reference liquid L of 6 g and containers 20 each containing reference liquid L of 8 g were prepared.

Figure 8A:
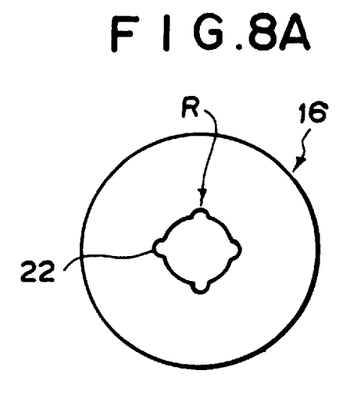
FIGS. 8A and 8B are plan views for illustrating the structures of the lid members employed in the experiment.
Figure 8B:
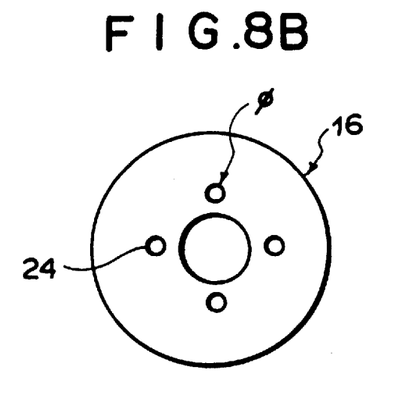

As the lid members 16, those having four semi-circular grooves 22 as shown in FIG. 8A, those having two semi-circular grooves 22, those having four circular through holes 24 as shown in FIG. 8B and those having two circular through holes 24 were prepared. The radii or diameters of the grooves or holes were as shown in the following table.

TABLE

| test # | #1 & 7 | #2 & 8 | #3 & 9 | #4 & 10 | #5 & 11 | #6 & 12 |
|---|---|---|---|---|---|---|
| R or φ | R0.1 mm | R0.25 mm | R0.8 mm | φ0.2 mm | φ0.5 mm | φ1.0 mm |
| area | 1.32 mm$^2$ | 1.88 mm$^2$ | 2.4 mm$^2$ | 0.52 mm$^2$ | 0.52 mm$^2$ | 1.11 mm$^2$ |
| number | 4 | 4 | 2 | 4 | 2 | 2 |
| % evp. | | | | | | |
| 6 g | 0.3817 | 0.3887 | 0.5765 | 0.2209 | 0.1819 | 0.3474 |
| 8 g | 0.2760 | 0.2820 | 0.3650 | 0.1660 | 0.1390 | 0.2410 |

In the table, "area" means measured areas of the grooves or holes and "number" means the number of the grooves or holes. Test numbers #1 to #6 were for containers containing reference liquid L of 6 g and test numbers #7 to #12 were for containers containing reference liquid L of 8 g.

Result of the Experiment

Figure 9A:
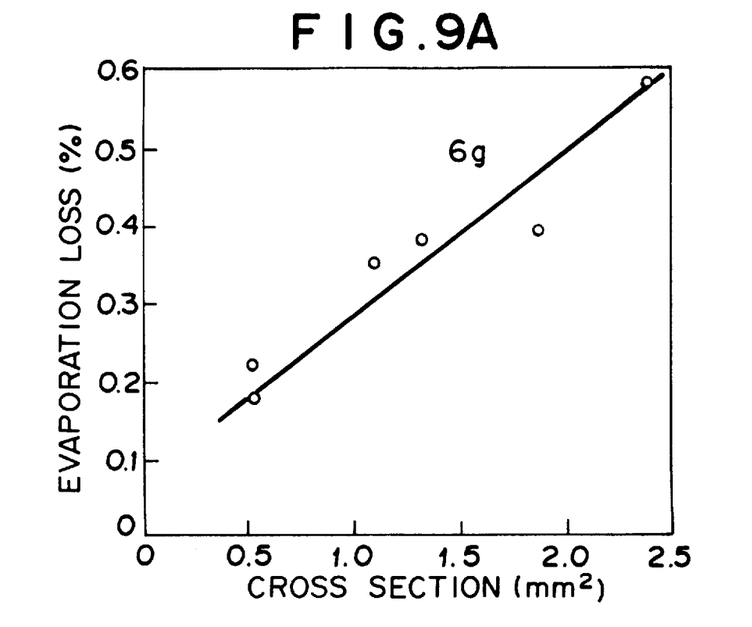
FIGS. 9A and 9B are graphs showing the result of the experiment.
Figure 9B:
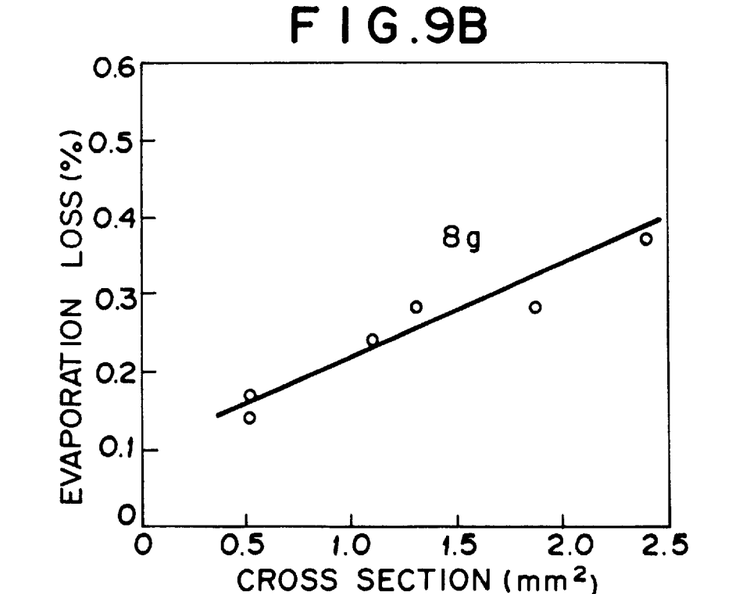

The result of the experiment were as shown in the above table and FIGS. 9A and 9B. FIG. 9A is for the containers containing reference liquid L of 6 g and FIG. 9B is for the containers containing reference liquid L of 8 g.

As can be understood from the table and FIGS. 9A and 9B, the evaporation loss increased substantially in proportional to the area of the communicating passages and the rate of increase was larger in the containers containing less liquid.

When the evaporation loss is not more than about 1% after elapse of 24 hours, it may be considered that concentration of the liquid is well prevented. In this regard, the evaporation loss was not more than 0.6% in any of the test samples, which proved the effect of the invention.

EXAMPLE 2

Employing the spotting tips employed in tests No.1 to No.12 in an electrolyte measuring system, measurement of electrolyte was repeated, and the evaporation loss was measured and occurrence of back flow was observed.

Result of the Experiment

The reference liquid L did not flow back into the spotting tip 12 or the nozzle 18 and the evaporation loss was not more than 0.7% with any of the spotting tips.

What is claimed is:

1. A spotting tip for use with a container the container defining an inside space and an outside space, having a mouth and containing a liquid in the inside space: the spotting tip acting to suppress evaporation of the liquid, prevent ingress of contaminating matter into the container and prevent spontaneous entry of the liquid into the spotting tip when the spotting tip is left in the liquid for prolonged periods of time, the spotting tip comprising:

a hollow tip body having an outer surface, an upper opening for fitting a liquid sucking means and a lower opening for insertion into the liquid through the mouth of the container;

a lid member having an upper surface, a lower surface for fitting over the mouth of the container and forming a substantially air-tight seal, and a passage from the upper surface to the lower surface, the passage having an inner surface for contacting a circumferential portion of the outer surface of the hollow tip body between the upper and lower openings to substantially close a space between the circumferential portion of the outer surface of the hollow tip body and the mouth of the container when the hollow tip body is inserted into the container to a predetermined depth; and at least one communicating passage for communicating the inside space and outside space and equalizing air pressure between the inside space and the outside space, the communicating passage being defined by a part of the outer surface of the hollow tip body and an adjacent part of the inner surface of the passage of the lid member, the communicating passage extending from the upper surface of the lid member to the lower surface of the lid member.

2. The spotting tip of claim 1, wherein the adjacent part of the inner surface of the passage of the lid member is a groove therein for forming the communicating passage.

3. The spotting tip of claim 2, wherein the groove is semicircular with a radius from about 0.1 to about 1.0 mm.

4. The spotting tip of claim 3, wherein the lower opening the hollow tip body is hydrophobic.

5. A spotting tip for use with a container, the container defining an inside space and an outside space, having a mouth and containing a liquid in the inside space; the spotting tip acting to suppress evaporation of the liquid, prevent ingress of contaminating matter into the container and prevent spontaneous entry of the liquid into the spotting tip when the spotting tip is left in the liquid for prolonged periods of time, the spotting tip comprising:

a hollow tip body having an outer surface, an upper opening for fitting a liquid sucking means and a lower opening for insertion into the liquid through the mouth of the container;

a lid member having an upper surface, a lower surface for fitting over the mouth of the container and forming a substantially air-tight seal, and a passage from the upper surface to the lower surface, the passage having an inner surface for contacting a circumferential portion of the outer surface of the hollow tip body between the upper and lower openings to substantially close a space between the circumferential portion of the outer surface of the hollow tip body and the mouth of the container when the hollow tip body is inserted into the container to a predetermined depth; and at least one communicating passage for communicating the inside space and outside space and equalizing air pressure between the inside space and the outside space, said at least one communicating passage comprising a groove selected from the group consisting of a groove formed in the outer surface of the hollow tip body to extend in a longitudinal direction of the hollow tip body from above the upper surface of the lid member to below the lower surface of the lid member, and a groove formed in the inner surface of the passage of the lid member to extend in a longitudinal direction of the passage of the lid member from the upper surface of the lid member to the lower surface of the lid member.

6. The spotting tip of claim 5, wherein the groove is semicircular with a radius from about 0.1 to about 1.0 mm.

7. The spotting tip of claim 5, wherein the lower opening of the hollow tip body is hydrophobic.

* * * * *